United States Patent
Tillmann et al.

(10) Patent No.: US 7,106,076 B2
(45) Date of Patent: Sep. 12, 2006

(54) DEVICE FOR THE SIMULTANEOUS APPLICATION OF ELECTRICAL SIGNALS AND MEASUREMENT OF THE ELECTRICAL POTENTIAL IN A SAMPLE

(75) Inventors: Axel Tillmann, Aldenhoven (DE); Andreas Kemna, Düsseldorf (DE); Egon Zimmermann, Inden-Altdorf (DE); Walter Glaas, Elsdorf (DE); Arre Verweerd, Aachen (DE)

(73) Assignee: Forschungszentrum Julich GmbH, Julich (DE)

(*) Notice: Subject to any disclaimer, the term of this patent is extended or adjusted under 35 U.S.C. 154(b) by 0 days.

(21) Appl. No.: 10/647,130

(22) Filed: Aug. 22, 2003

(65) Prior Publication Data
US 2004/0222805 A1 Nov. 11, 2004

(30) Foreign Application Priority Data
Aug. 23, 2002 (DE) ................ 102 38 823

(51) Int. Cl.
*G01R 27/08* (2006.01)
(52) U.S. Cl. ........................... 324/715; 324/713
(58) Field of Classification Search ............. 324/715, 324/691, 713, 723, 724, 354, 355, 72.5
See application file for complete search history.

(56) References Cited

U.S. PATENT DOCUMENTS

| | | | | |
|---|---|---|---|---|
| 4,219,776 A | * | 8/1980 | Arulanandan | 324/323 |
| 4,654,598 A | * | 3/1987 | Arulanandan et al. | 324/354 |
| 5,346,307 A | * | 9/1994 | Ramirez et al. | 374/136 |
| 5,574,371 A | * | 11/1996 | Tabanou et al. | 324/324 |
| 5,841,282 A | * | 11/1998 | Christy et al. | 324/347 |
| 6,002,257 A | * | 12/1999 | Thomas et al. | 324/324 |
| 6,384,614 B1 | * | 5/2002 | Hager et al. | 324/754 |
| 6,507,201 B1 | * | 1/2003 | Tominaga | 324/715 |

FOREIGN PATENT DOCUMENTS

| DE | 197 07 788 | 7/1998 |
|---|---|---|
| DE | 198 37 828 | 4/2000 |

* cited by examiner

*Primary Examiner*—Anjan Deb
*Assistant Examiner*—John Teresinski
(74) *Attorney, Agent, or Firm*—Andrew Wilford

(57) ABSTRACT

An electrode, in the form of a spike, for insertion into a sample, has a large-area jacket adapted for applying an excitation current to the sample and a small-area tip electrically decoupled from the jacket, at which a potential measurement is made.

7 Claims, 4 Drawing Sheets

DEVICE FOR THE SIMULTANEOUS APPLICATION OF ELECTRICAL SIGNALS AND MEASUREMENT OF THE ELECTRICAL POTENTIAL IN A SAMPLE

CROSS REFERENCE TO RELATED APPLICATIONS

This application claims the benefit of the filing date of 23 Aug. 2002 of the German application 102 38 823.7 under 35 USC 119 and the International Convention.

FIELD OF THE INVENTION

Our present invention relates to a device for the simultaneous feeding of electrical signals to a sample and for the measurement of electrical potential in a sample. In particular the invention relates to a device which is particularly suitable for determining electrical conductivity or resistivity of a ground sample and especially for use in tomography with respect to such samples, i.e. evaluation of ground samples by determining the conductivity or resistivity of different sections through the sample.

BACKGROUND OF THE INVENTION

The measurement of potential differences in a sample is a prerequisite, inter alia, to the calculation of the electrical conductivity of the sample or a region or cross section of the sample. For this purpose the sample is generally excited with an electrical current. From the measured voltage drop and the amplitude of the current flow, the electrical resistance and its inverse, the conductivity of the sample can be calculated.

Various measuring units have been used in the art for the determination of resistivity or conductivity and methods of measuring the electrical conductivity are known.

Basically these units comprise at least one electrode pair. The so-called Kohlrausch arrangement encompasses two mutually opposite solid body electrodes, for example of carbon or platinum or platinized metal. The form of these electrodes can vary.

For carrying out the electrical conductivity measurement an alternating current voltage is applied to the electrode and current is thereby fed to an electrically conductive sample via electrodes. The resulting electrode potential is measured by the same electrodes as supplied the current.

A simple embodiment for carrying out such measurement uses so-called pole-to-pole measurements which are practiced with two electrodes. With these electrodes the current and the potential difference between the two electrodes are measured.

A drawback of this system is that the measurement results are influenced by the polarization effect at the boundary layers between the electrodes of the sample. In special cases with ground samples and other heterogeneously structured samples there arises between the sample and the electric current feeding electrodes high resistances which are functions of the point at which the electric current is fed to the sample.

A four-point method (four electrode method) of measuring the potential in soil samples can also be practiced. In that case, two electrodes are used to feed electrical signals into the sample. The electrodes serve at any given point in time either for applying the excitation alternating current or for the high ohmic measurement of the potential. From the known amplitude of the current flow and the measured potential difference, the resistance or the conductivity of the sample can be readily calculated. The transition resistance and other potential drops due to polarization effects at the interface between the sample and the electrode are not determined with such measurements.

A drawback of the prior art system for simultaneous measurement of the potential difference and application of electric current to the sample at two closely adjoining electrodes or two surfaces of the same electrode which closely adjoin one another is that the electrode must have a complex and expensive construction. With heterogeneously structured and dense samples, for example, soils, aquifers, rock and ore strata, a large number of electrodes must be employed in such samples. For measurements which are to determine the conductivity of specific areas and/or tomographic measurements which are to determine conductivity or resistivity of sections through the sample, a large number of different current-supply and measurement electrodes must be provided with different current-supply and measurement configurations. The measurement arrangements for complex samples especially those utilized for geophysical or geoelectrical analyses are known from German patent document 198 37 828.

There are, however, different drawbacks of such systems depending upon the measurement method. In principle, of course, for all measurements which are to be carried out utilizing a common electrode for application of the electric current and measurement of the potential, for example in the two electrode method, measurement errors arise because of the high variable and unknown transition resistances between the electrode and the sample, especially when the electrode is driven into the ground.

Four electrode measurement systems are either expensive or complex to use because installation becomes a major factor. From each measurement position, an additional electrode must be employed and the distances from each electrode to another electrode may not be precisely defined.

For area-like and tomographic measurements utilizing sequential feed of electric current through a sample, measurement errors occur as a result of polarization effects at the electrodes since in these methods the potential measurements are effected at the moment that the current is applied at the very same electrode surfaces and thus with polarized electrodes.

OBJECTS OF THE INVENTION

It is therefore the principal object of the present invention to provide a device which can apply optional electric excitation signals to a sample simultaneously with a potential measurement therein whereby the disadvantages mentioned above and particularly the polarization phenomenon, can be avoided.

Another object of the invention is to provide a device for the measurement of electric potential in a sample in which measurement errors resulting from polarization effects are excluded in a simple manner.

Still another object of this invention is to provide an improved device for measuring electrical potential in a sample and particularly in a ground sample or other geologically significant sample, which permits tomographic evaluation of the sample at least with respect to conductivity measurement in an improved manner.

SUMMARY OF THE INVENTION

These objects and others are attainable in accordance with the invention in an apparatus or device which comprises:

an electrode body formed with two electrically separate surfaces positioned to contact simultaneously a sample;

a electrical excitation source connected to one of the surfaces for feeding an electrical excitation signal to the sample; and an electrical potential measuring unit connected to the other of the surfaces for measuring an electrical potential in the sample resulting from application of the electrical excitation signal to the sample.

With the device according to the invention, the electrode body has two electrically decoupled surfaces in a single electrode structure, one of which serves for applying electrical excitation signals of any optional kind to the sample while the other serves for a simultaneous potential measurement. Since the two surfaces are electrically decoupled from one another, they can be provided in a single body without the polarization of the surface supplying the excitation signal affecting the measurement.

Advantageously the surface area of the surface for measuring the potential is smaller, particularly by a factor of at least 10, than the surface area of the surface for applying the excitation signal. As a result, the interface resistance at the boundary layer with the sample can be held low and the measurement of the potential can be highly accurate in a localized sense.

The device can have a tip forming the electrode surface for potential measurement and it can be driven into the ground. The tip, which can be pointed to permit the electrode to penetrate easily into the ground can be spaced from a jacket of the electrode which can feed the electrical excitation signal into the sample.

The electrode body can then have the configuration of a spike or lance with electrically decoupled surfaces, one of which serves for electrical excitation while the other serves for the measurement of the potential. The tip preferably forms the surface for the potential measurement. The decoupling can be effected by an annular insulator ring between the shell and the tip.

When the jacket of the spike forms the electrode for feeding the electrical excitation signal into the sample, the coupling of the jacket to the sample will depend upon the depth of penetration of the spike into the sample. The excitation current may be an alternating current which is supplied by the variable coupling surface.

The device of the invention is of simple construction and measurement errors resulting from polarization effects can be excluded by its use. To emplace the electrode spike, only half the time previously required for electrode positioning is found to be necessary in accordance with the invention. For a given sample area, the measurements can be accelerated and, particularly complex samples, like those of ground regions, can be investigated quickly and with a comparatively small number of electrodes. Of course in the case of more complicated sampled regions, complex arrays of electrodes according to the invention can be used.

The measurements are taken upon the supply of electrical excitation signals to the sample. The electrical excitation signals can be constant alternating current or direct current signals as well as alternating or direct voltages with variable current amplitudes, as long as the application of the signal is applied through the jacket of the electrode spike. When reference is made here to "optional signals" we intend to signify that the choice of the signal wave form or pattern will depend upon the function and convenience factors. For example, the signals may be sinusoidal or rectilinear or square wave signals or can have any other shape with ramps, steep flanks, straight flanks or curved flanks. The current in all cases, however, should be supplied over a relatively large area to minimize the interfacial resistance, i.e. the resistance at the interface between the jacket and the sample.

The electrode spike can advantageously have a tip which is composed of solid metal and whose outer periphery is used for measurement of the potential in the sample. The prerequisite for measurement of the potential is the contact of the point with the sample. The point can thus be driven into relatively dense samples, for example the ground aquifers and the like.

The electrode for applying the electrical excitation signal can be a metallic tubular jacket. A jacket of this type is particularly suitable for applying an electrical current to such samples. The jacket can thus be composed of a metallic tube or pipe.

Preferably the tip or point of the spike, for measuring the potential difference, is composed of metal which is more noble than that forming the jacket of the spike. In the case of electrical excitation where the excitation signal is not a constant electrical signal, the phase shift between the electrical signal applied and the measured potential at the boundary layer between the electrode for measuring the potential and the sample is minimal.

The electrode spike jacket and the electrode spike point can be separated by an insulating material. the insulating material can be in the form of an insulating ring interposed between the spike tip and the spike jacket and can electrically separate these parts of the electrode from one another.

For coupling the tip of the electrode spike, as the potential measuring electrode, to further circuitry for evaluating the measured potential and especially for determination of conductivity in the sample, a flexible conductor can be used and can pass through the interior of the electrode spike to terminate in a coaxial connector at the top of the spike. The coaxial connector, e.g. a coaxial plug, can be connected to the circuitry standard coaxial coupling.

The spike can be a solid metal tube which has at one end the aforementioned tip, separated from the solid metal tube by the compression resistance annular insulator. In an alternative construction, the tip may have a solid metal rod extending upwardly in the jacket and insulated from the jacket by a tubular insulator. That rod may be formed in one piece with a solid tip. Instead of a rod, a solid metal tube may also be used. In this case, the rod or tube at its top may be connected to the coaxial connector. Such electrodes have been found to be especially suitable for dense samples like dense soil.

When a flexible conductor is not used in the electrode spike, the upper end of the solid metal tube or rod of the pointed tip can be connected to a flat strip plug or like connector for connection to the evaluating or processing circuitry. Such a flat strip plug has been found to be particularly advantageous for the application of alternating current to the jacket of the electrode when an alternating current excitation is desired.

All of the insulators used in the system of the invention should be high compressive strength synthetic resins capable of withstanding impact.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
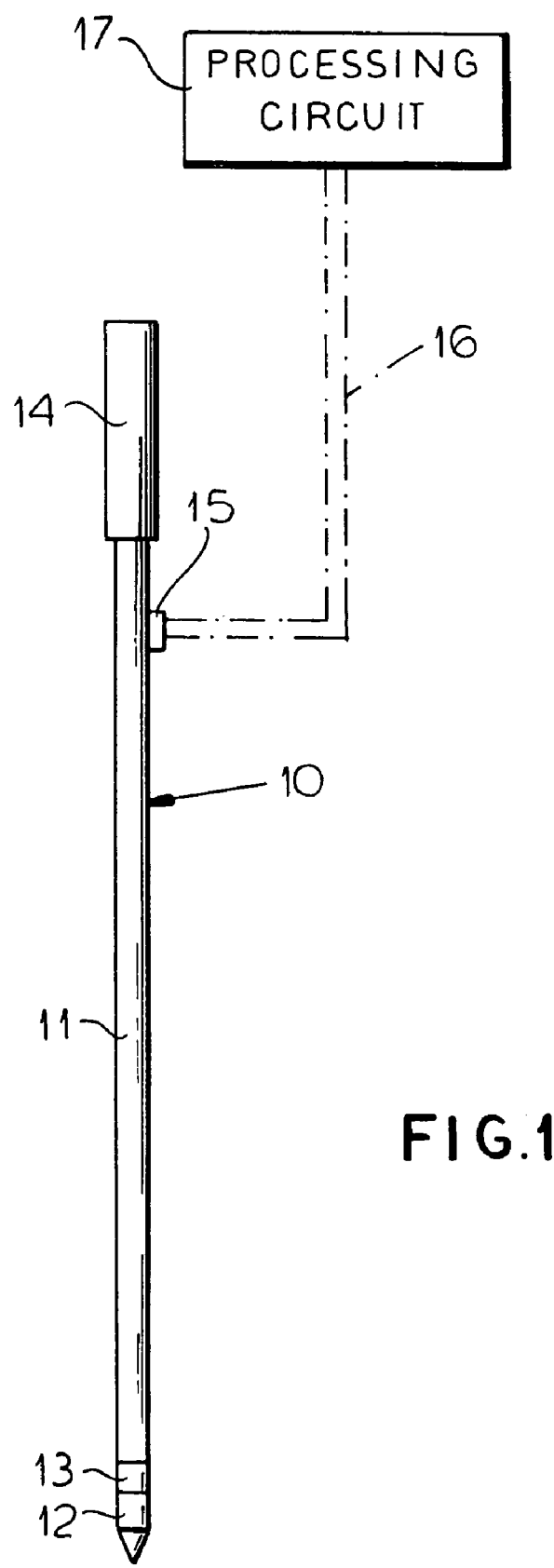
FIG. 1 is an elevational view in highly diagrammatic form illustrating an electrode spike in accordance with the invention and the evaluating circuitry therefor.

FIG. 1 shows an electrode spike 10 having a conductive jacket 11 separated form a solid pointed tip 12 by an insulating ring 13 capable of withstanding compression. At the upper end of the spike 10 is a solid impact piece 14 which can be hammered to drive the spike into the ground. A coaxial connector 15 at the upper end of the jacket 11 can be connected by a coaxial cable to the signal processing circuit 17.

Figure 2:
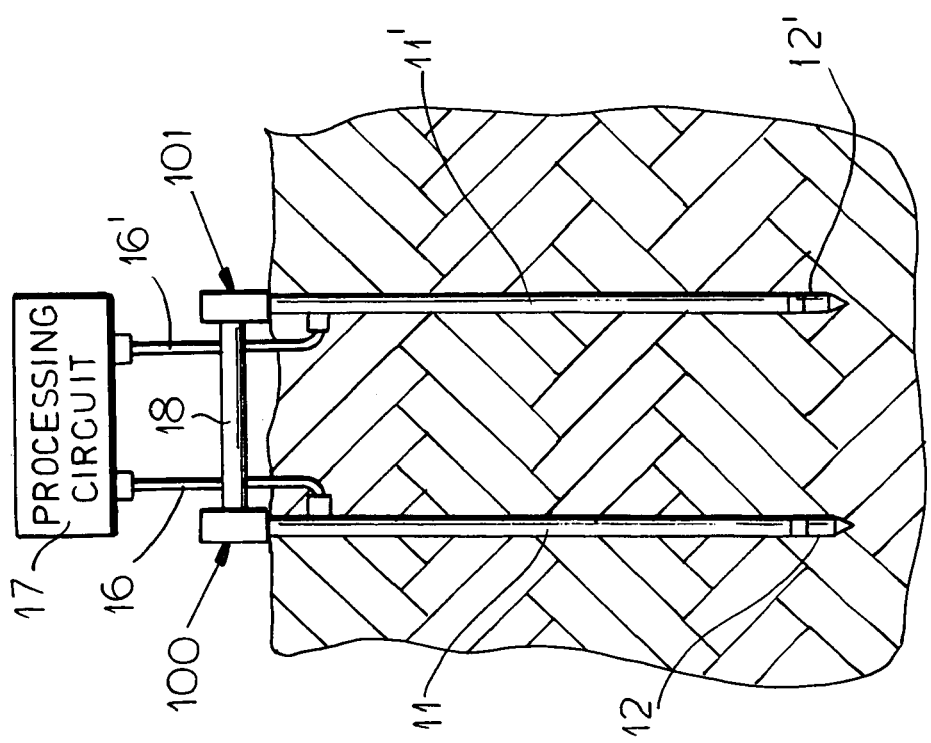
FIG. 2 is a diagram of an apparatus showing the application of the system to a ground sample.

In FIG. 2, two such spikes 100 and 101 are driven into a sample in which the conductivity is to be measured. The spikes can be connected together, e.g. from a framework 18 and each of the electrodes may be connected by the appropriate coaxial cable 16, 16' to the processing circuit 17.

With the sample, an excitation current is applied between the jackets 11, 11' of the two electrodes while the potential difference is measured between the two electrode tips 12 and 12'.

Figure 3:
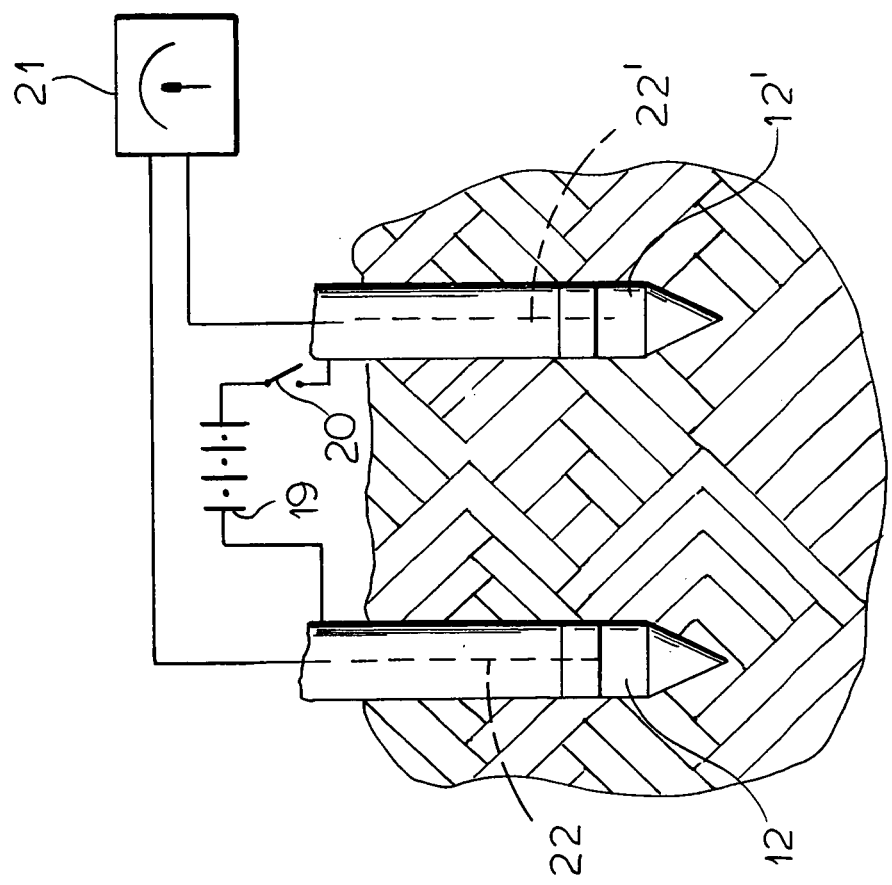
FIG. 3 is another diagram illustrating the principle of the invention.

This is shown in greater detail in FIG. 3 where the sample is again a ground region forming part, for example, of an aquifer. Here the excitation source is shown as a direct current source 19 provided with an electronic switch 20. The potential measuring circuit is represented by the meter 21 and is shown to be connected to the electrode tip 12 and 12' via conductors 22 and 22' running down the center of the respective electrodes.

Figure 4:
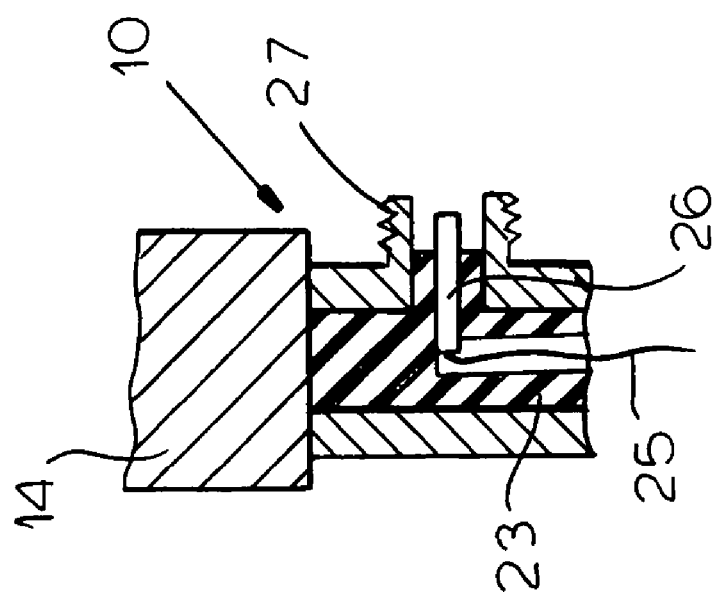
FIG. 4 is a cross sectional view showing a top portion of an electrode in accordance with the invention.
Figure 5:
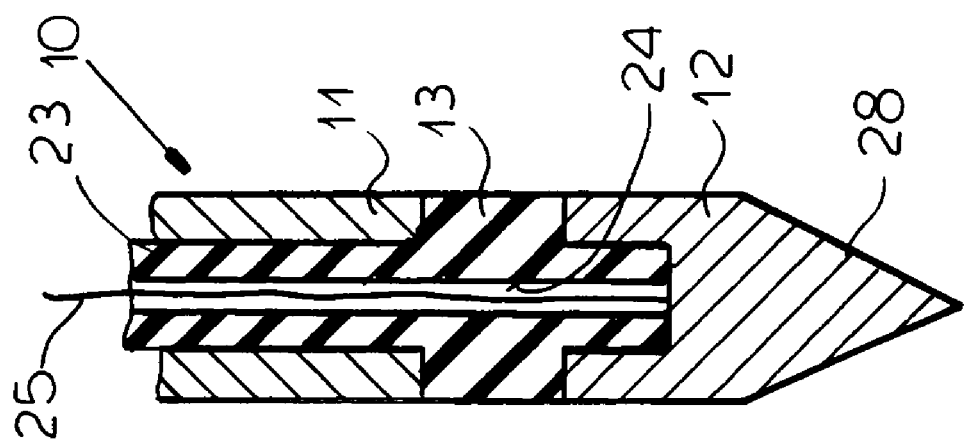
FIG. 5 is a cross sectional view showing the bottom portion of the same electrode.

In FIG. 4 and 5 we show the upper and lower ends of an electrode spike 10 which can have the solid metal tip 12 previously described which can be composed of a metal more noble than the metal of a jacket 11 formed by the metal tube. Here the insulating ring 13 forms part of a tubular insulator 23 which extends upwardly through the tube 11 and has a bore 24 through which a flexible wire 25 runs to a pin 26 of a coaxial connector 27 whose outer portion is formed on the metal tube 11. The solid impact member 14 is likewise visible in FIG. 4. The tip 12 has a pointed end 28 to facilitate the driving of the spike into the ground.

Figure 6:
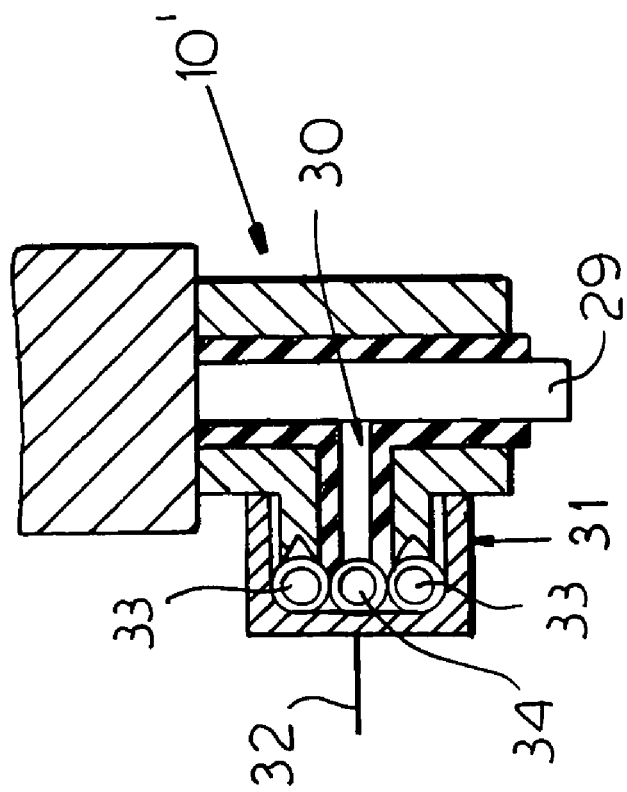
FIG. 6 is a cross sectional view of a top portion of another electrode in accordance with the invention.
Figure 7:
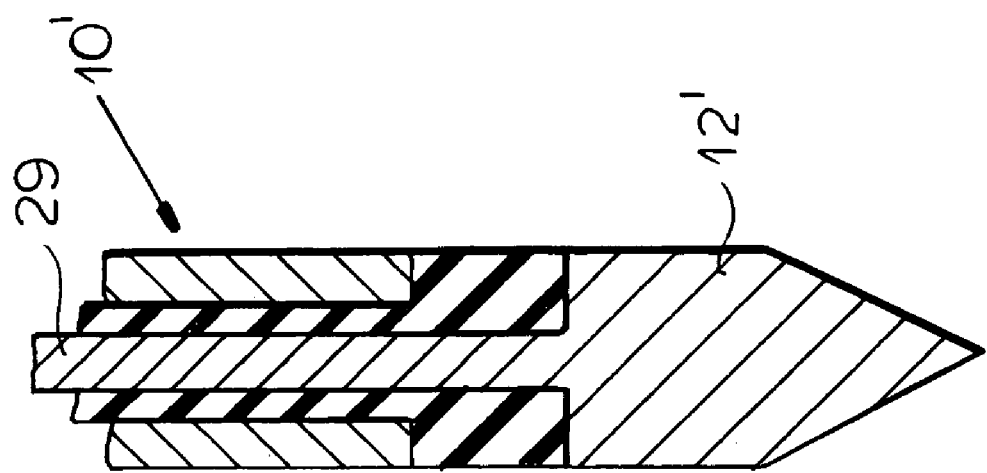
FIG. 7 is a cross sectional view of the bottom portion thereof.

As has been described, the jacket 11 serves for applying the excitation current to the ground sample while the tip 12 serves for measuring the potential difference. In FIGS. 6 and 7, another electrode structure 10' has been shown in which the tip 12' is likewise a solid metal tip and has, instead of the flexible conductor 25, a solid metal rod 29 or solid metal tube which runs to the connecting lead 30 which, in turn, is joined to a flat strip connector 31. The flat strip connector 31 is connected, in turn, to the processing circuit at 32 and has contacts 33 for applying the excitation signal and a contact 34 for deriving the potential measurement in the manner described.

In the embodiment of FIGS. 4 and 5, the tubular insulating member 23 fills the space in the jacket 11 to increase the mechanical stability of the spike.

When the electrode spikes of the invention are used in pairs, the conductivity profile of the sample between them can be readily measured by the application of the excitation current and the measurement of the potential difference. A multiplicity of such electrodes can be used when a conductivity profile in three dimensions is desired. The processing circuit 17 can include, therefore, a current source, the measuring instruments for current amplitude and voltage measurement and a programmable controller for the sequential current feed to different electrode spikes, and an output unit for recording, registering or displaying the conductivity. A microprocessor can be used for converting analog signals to digital signals for storage of data, for further computing operations and/or for outputting measured values. The electrical resistance or, its reciprocal, the conductivity of the sample may be measured.

The flat strip plug 31 of FIG. 6 may be designed for the correct-pole connection of a plug or socket. This has been found to be especially important in the field. However, a coaxial connector can be used with the embodiment of FIG. 6 as well. The impact member 14 may be linked to serve as a handle for insertion of the electrode into the sample.

The electrodes of the invention, can be employed with a suitable advantage for high-speed tomography measurements of conductivity distribution in complex samples in which the excitation signals are supplied selectively to the electrodes and the respective potential differences are measured and the potential differences are registered in proportion to the applied electrical excitation signal. The electrical signals can be transformed into orthogonal electrical signals so that the conductivity cross section of the sample can be ascertained with precision. With a four-electrode arrangement, for example, a considerable time-saving is obtained since, with the system of the invention, only half the number of the electrode bodies which must be handled can provide the desired information.

The invention has been found to be advantageous as well because it ensures that the spacing between the excitation electrode surface and the potential measurement electrode surface is always constant and can be relatively small, as is important for geophysical applications.

For all measurements in which an electric current is applied simultaneously with potential measurements, errors are eliminated which may result from contact resistance since there is practically no current flowing at the surfaces at which tips for measuring the potential contact of the sample and thus there is no potential drop resulting from such a contact resistance. Polarization effects also do not arise.

A further advantage is the lower cost of the electrodes of the invention by comparison with the special electrodes which had to be used heretofore to avoid the problem of induced polarization.

The invention enables minimization of the phase shift of an alternating current excitation signal so that the phase shift at the interface between the tip of the spike and the sample can be minimized. This is especially the case when the metal chosen for the material of the tip is a noble metal, for example, platinum or platinum group metal. For the portion of the electrode utilized to apply the alternating current to the sample, this expense is not necessary since its influence on the phase of the alternating current is irrelevant.

Because of the separation of the functions of applying the excitation current and measuring the potential to two different surfaces of the spike, the measurement electrode can be a much smaller area and this is of advantage when a noble metal is used.

The electrode spike and the devices of the invention can be used in a wide range of applications including:

Determining the concentration of soluble substances in the ground and in ground water courses from the conductivity distribution.

Monitoring chemical processes by measuring the time and special variations in the conductivity distribution (for example precipitation reactions).

Determining trace and electrical anomalies including the presence of metallic bodies, ores, conductors, archeological objects, etc.

Monitoring preferred flow and transport paths in porous media (the ground, aquifers, mineral deposits and laboratory applications.

monitoring the distribution of agricultural chemicals.

Surfaces in connection with catastrophe management and industrial accidents.

Contamination of industrial sites.

Monitoring on-site and laboratory processes in connection with the transport of substances of porous media.

Determination of particle and colloid transports.

Research as to the distribution and occurrence of traces of poorly-conducting liquids in the ground and in aquifers including the formation of water filaments on particles to determine contaminant distribution, sanitary problems, waste dump leakage, failures of dikes, the ability of strata to take up and hold water in arid or semiarid regions, the monitoring of fronts between salt water and sweet water in agriculture and other echo systems.

The electrode spike can be used in medicine as well or the measurement of characteristics in the body, of course in a miniature configuration and can be used in food technology to test food properties.

Other configurations of the electrode may also be employed. The electrode can be used especially in the methods described in our commonly owned concurrently filed copending application Ser. No. 10/647,095 corresponding to German application 102 38 824.5 of 23 Aug. 2002.

We claim:

1. A device for measuring electrical potential comprising:
   an electrode body in the form of a spike adapted to be driven into the ground and formed with two electrically separate surfaces positioned to contact the ground simultaneously the ground forming a sample;
   an electrical excitation source connected to one of said surfaces for feeding an electrical excitation signal to said sample, said one of said surfaces being a jacket of said body in the form of a metal tube, the other of said surfaces for measuring an electrical potential in the ground being formed upon a pointed solid metal tip of said spike adapted to be driven into the ground; and
   an electrical potential measuring unit connected to the other of said surfaces for measuring an electrical potential in said sample resulting from application of said electrical excitation signal to said sample, the tip of said spike being composed of a more noble metal than said jacket.

2. The device defined in claim 1 wherein the jacket is separated from the tip by an annular insulator.

3. The device defined in claim 2, further comprising a flexible electrical conductor extending upwardly through said tube and connected to said tip.

4. The device defined in claim 3, further comprising an insulator extending through said tube and separating said flexible electrical conductor from said jacket.

5. The device defined in claim 2, further comprising a solid metal rod or tube extending upwardly from said tip through said jacket to supply an electrical potential measurement to an electric circuit.

6. The device defined in claim 5, further comprising an insulating tube surrounding said solid metal rod or tube for insulating said solid metal rod or tube from said jacket.

7. A device for measuring electrical potential in the ground, comprising:
   an electrode body in the form of a spike adapted to be driven into the ground and having an electrically conductive metal jacket and an electrically conductive metal point electrically insulated from the jacket and composed of a metal more noble than the metal of said jacket;
   an electrical excitation source connected to the jacket for feeding an electrical excitation signal to the ground; and
   an electrical potential measuring unit connected to said point for measuring electrical potential in the ground resulting from application of said electrical excitation signal thereto.

* * * * *